United States Patent [19]

Fujiu et al.

[11] 4,437,192
[45] Mar. 20, 1984

[54] IMPLANTS OF BIOLOGICALLY ACTIVE GLASS OR GLASS CERAMIC CONTAINING TITANIA

[75] Inventors: Takamitsu Fujiu, Tokyo; Makoto Ogino; Michio Kariya, both of Yokohama; Takeo Ichimura, Tokyo, all of Japan

[73] Assignee: Nippon Kogaku K.K., Tokyo, Japan

[21] Appl. No.: 476,041

[22] Filed: Mar. 16, 1983

Related U.S. Application Data

[63] Continuation of Ser. No. 270,588, Jun. 4, 1981, abandoned.

[30] Foreign Application Priority Data

Jun. 11, 1980 [JP] Japan .................. 55-77841

[51] Int. Cl.³ .............................. A61F 1/00; A61F 1/24
[52] U.S. Cl. ........................................ 3/1.9; 128/92 C; 428/432; 428/433; 428/434; 501/18; 501/21; 501/24; 501/25; 501/59; 501/63; 501/64; 501/65; 501/67
[58] Field of Search ................. 501/5, 18, 21, 24, 25, 501/58, 59, 63, 64, 65, 67; 3/1.9; 128/92 C; 428/432, 433, 434

[56] References Cited

U.S. PATENT DOCUMENTS

| | | | |
|---|---|---|---|
| 2,347,187 | 4/1944 | Frost | 501/58 X |
| 2,660,531 | 11/1953 | Fraser et al. | 501/18 |
| 3,463,646 | 8/1969 | Little et al. | 501/24 |
| 3,881,945 | 5/1975 | Trojer et al. | 501/5 X |
| 3,987,499 | 10/1976 | Scharbach et al. | 128/92 C |
| 4,004,935 | 1/1977 | Grosvenor et al. | 501/18 |
| 4,103,002 | 7/1978 | Hench et al. | 428/432 X |
| 4,120,730 | 10/1978 | Trojer et al. | 501/5 X |
| 4,168,326 | 9/1979 | Broemer et al. | 3/1.9 |
| 4,171,544 | 10/1979 | Hench et al. | 3/1.9 |
| 4,234,972 | 11/1980 | Hench et al. | 3/1.9 |
| 4,365,356 | 12/1982 | Broemer et al. | 3/1.9 |

FOREIGN PATENT DOCUMENTS

2546824   5/1982   Fed. Rep. of Germany .

OTHER PUBLICATIONS

Hench, L. L. "Ceramic Implants"-Resour. Recovery Proc. ASME, 1975 pp. 197-205.

Primary Examiner—Helen M. McCarthy
Attorney, Agent, or Firm—Fitzpatrick, Cella, Harper & Scinto

[57] ABSTRACT

A biologically active glass and class-ceramic composition useful for making surgical and dental implants comprising, by mol %,:

| | |
|---|---|
| $SiO_2$ | 35~60 |
| $B_2O_3$ | 5~15 |
| $Na_2O$ | 10~30 |
| CaO | 5~40 |
| $TiO_2$ | 0.5~10 |
| $P_2O_5$ | 0~15 |
| $K_2O$ | 0~20 |
| $Li_2O$ | 0~10 |
| MgO | 0~5 |
| $Al_2O_3 + ZrO_2 + Nb_2O_5$ | 0~8 |
| $La_2O_3 + Ta_2O_5 + Y_2O_3$ | 0~8 and |
| $F_2$ | 0~15. |

3 Claims, 3 Drawing Figures

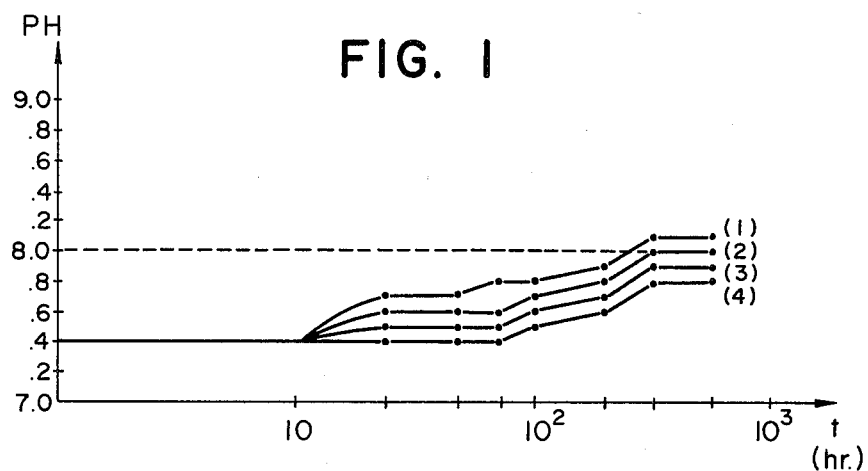
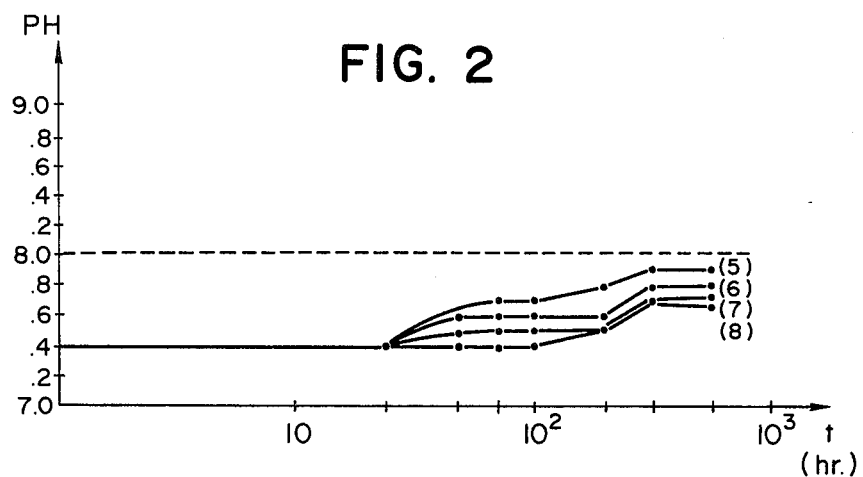
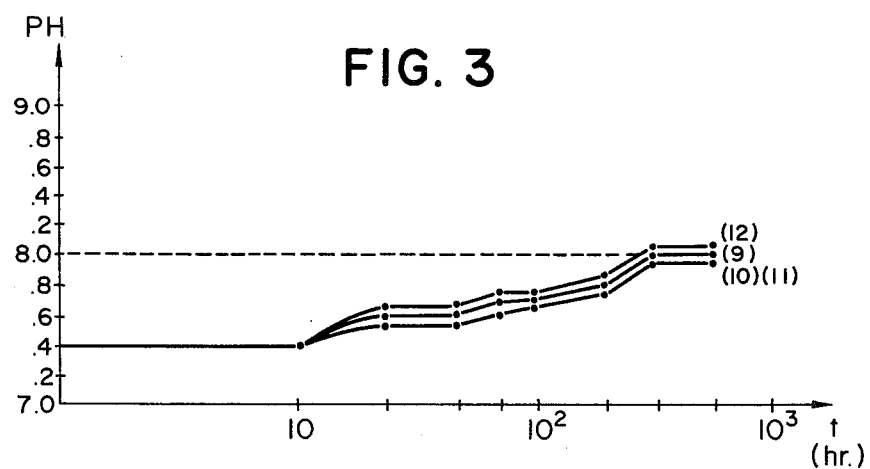

IMPLANTS OF BIOLOGICALLY ACTIVE GLASS OR GLASS CERAMIC CONTAINING TITANIA

This application is a continuation of application Ser. No. 270,588 filed June 4, 1981, now abandoned.

BACKGROUND OF THE INVENTION

1. Field of the Invention

The present invention relates to a biologically active glass and glass-ceramic composition and an implant coated with the composition.

2. Description of the Prior Art

In the art there are known biologically active glass and glass ceramics which are able chemically to combine directly with hard tissues, in particular, bones in a living body. Upon contacting the body fluids in vivo, the biologically active material reacts and bonds to bones. The mechanism of the reaction between the material and the hard tissue in a living body is described in detail in a publication, J. Biomed. Mater. Res. Symp. No. 2 (Part 1), 117-141 (1971). In summary, the mechanism is as follows:

Constituents of the material such as Na, Ca, P, B and Si are dissolved out from the surface of the material into the body fluid as the respective ions thereby forming micro pores on the surface. P and Ca ions derived from the biologically active material and also P and Ca ions derived from the living body itself owing to its bone making ability are gradually deposited in the formed pores and crystallized into hydroxylapatite which is the main substance of bone. Thus, a direct and chemical bonding is obtained between the biologically active material and the bone.

On the other hand, it is known that no practically useful implant can be produced using only such a biologically active material because of its insufficient mechanical strength. For a solution to the problem, the employment of a metal core having a high mechanical strength sufficient to resist the load normally applied thereto in use, with a coating of such biologically active glass or glass ceramics, has been proposed, and clinical tests have been made for implants thus fabricated.

To apply the coating of biologically active material to the metal core there have been used various methods in which the biologically active glass and glass ceramics have to be molten as a rule. In this case, a preferred coating process is an enamelling process which enables a uniform coating to be realized. However, use of the enamelling process is allowed only when the biologically active material and the metal core to be coated with the material have nearly equal coefficients of thermal expansion and the biologically active material has a relatively low melting point. If the biologically active material and the metal core have different coefficients of thermal expansion, then cracks will easily be developed in the coating layer after cooling. Also, if the biologically active material is not fusible at relatively low temperatures, then the high temperature molten glass or glass ceramics may damage the core and furthermore, the coating may be contaminated with metal ions.

From the above it is concluded that biologically active glass and glass ceramics to be applied to a metal core to form an implant are required to satisfy the following requirements all at once:

(1) To have an adequate reactivity to allow leaching of various ions from its surface;

(2) To have a coefficient of thermal expansion substantially equal to that of the metal core and (3) To have a relatively low melting point.

All of the known biologically active glass and glass ceramics can not satisfy the above requirements all at once. For example, mention may be made of those biologically active glass and glass ceramics as disclosed in Japanese Patent Application Laid Open No. 145,394/1978 the counterparts of which are U.S. Pat. Nos. 4,159,358 and 4,234,972. Within the range of ingredient contents allowable for composing the biologically active material specified therein, it is not possible to obtain many combinations of the reactivity and coefficient of thermal expansion. In more detail, if the composition of the biologically active material is selected in such manner as to give the material a coefficient of thermal expansion substantially equal to that of the metal core to be coated with the material, then the reactivity of the material is determined thereby. It is no longer possible to determine the reactivity independently of the selected coefficient of thermal expansion.

When one wishes to form an implant by coating a metal core with any known biologically active material, the coefficient of thermal expansion of the coating material must first be determined, considering the coefficient of thermal expansion of the core. Since, as noted above, the reactivity of the material is determined by the selected coefficient of thermal expansion, there is left almost no possibility of free selection of the reactivity after the selection of coefficient of thermal expansion for biologically active glass and glass ceramics hitherto known. However, selection of reactivity is of great importance for usefulness of a biologically active implant as will be seen from the following description.

We, the inventors of the present invention, have conducted a number of experiments on the biologically active glass and glass ceramics proposed by the prior invention, that is, the aforementioned Japanese Patent Application Laid Open No. 145,394/1978 to examine the strength of chemical bonding between the material and various bones. In these experiments the vivo, the known biologically active materials were implanted in thighbones of rats, craniums of rabbits and jawbones of dogs. The results obtained from these animal experiments demonstrated the fact that the chemical bonding strength between the biologically active material and bones is variable according to the kind of test animal and also, even in the same kind of animal, according to age, and condition of the animal and also the position where implantation was made. This difference in the bonding strength obviously resulted from the difference in bone forming ability between different living bodies and also between different parts of the body.

As previously described, when the biologically active material is implanted in a living body, there takes place on the surface of the material a chemical reaction by which ions are leached from the surface and thereby micro pores are formed on the surface. With the proceeding of the surface reaction, new bone is formed owing to the bone forming ability of the living body and the micro pores in the material are gradually filled up with the new bone. A perfect and strong biologically active material-to-bone bond can be attained only when the surface reaction proceeds at a speed substantially equal to the bone making speed. Therefore, in case that the reactivity of the used biologically active material can not follow the bone forming ability of the body part where the material was implanted, it will result in poor bonding strength.

Accordingly, for clinical use of an implant having a coating of biologically active glass or glass ceramics, it is essential to employ such biologically active material, the reactivity of which corresponds to the bone forming ability of the body part where the implant is to be implanted.

As a result of the aforementioned surface reaction of the biologically active material in vivo, ions such as Na, Ca, P, B and Si are leached from the surface. The amount of leaching ions is predominant in Na and Ca. Leaching of other ions such as P, B and Si is gradual and begins after the glass structure has been destroyed to some extent as a result of leaching of Na and Ca ions. This means that evaluation of the reactivity of a biologically active material to a living body can be conducted simply by observing the change of pH primarily attributable to the leached Na ion. More particularly, the material is brought into a simulated physiological solution particularly prepared for this purpose and it is held immersed in the solution long enough to observe the change in pH of the solution resulting mainly from the leaching of Na ion from the material in the solution. In this manner, the evaulation of reactivity of the material to a living body can be performed by a simple pH test in vivo.

SUMMARY OF THE INVENTION

Accordingly, it is an object of the invention to provide biologically active glass and glass ceramics with which one can select at will any desirable combination of coefficient of thermal expansion and reactivity regarding the reaction by which ions are leached from the surface of the material when contacted with body fluids in a living body, and also which have a relatively low melting point.

It is another object of the invention to provide improved metal implants covered with a coating of such biologically active glass or glass ceramics.

To attain the above objects according to the present invention there is provided a biologically active glass and glass-ceramic composition essentially comprising, by mol %,:

| | |
|---|---|
| $SiO_2$ | 35~60 |
| $B_2O_3$ | 5~15 |
| $Na_2O$ | 10~30 |
| $CaO$ | 5~40 |
| $TiO_2$ | 0.5~10 |
| $P_2O_5$ | 0~15 |
| $K_2O$ | 0~20 |
| $Li_2O$ | 0~10 |
| $MgO$ | 0~5 |
| $Al_2O_3 + ZrO_2 + Nb_2O_5$ | 0~8 |
| $La_2O_3 + Ta_2O_5 + Y_2O_3$ | 0~8 |
| $F_2$ | 0~15 |

Also, there is provided an implant covered with a coating of the above defined biologically active material.

There has thus been outlined rather broadly the more important features of the invention in order that the detailed description thereof that follows may be better understood and in order that the present contribution to the art may be better appreciated. There are, of course, additional features of the invention that will be described hereinafter and which will form the subject of the claims appended hereto. Those skilled in the art will appreciate that the conception upon which this disclosure is based may readily be utilized as a basis for the designing of other structures for carrying out the several purposes of the invention. It is important, therefore, that the claims be regarded as including such equivalent constructions as do not depart from the spirit and scope of the invention.

BRIEF DESCRIPTION OF DRAWINGS

Specific embodiments of the invention have been chosen for purposes of illustration and description, and are shown in the accompanying drawings, forming a part of the specification wherein:

FIG. 1 is a graph showing the change of pH with time for a first group of embodiments of the composition according to the invention shown in Table 1;

FIG. 2 is a similar graph for a second group of embodiments shown in Table 2; and FIG. 3 is a similar graph for a third group of embodiments shown in Table 3.

DETAILED DESCRIPTION OF THE INVENTION

We have found that the reactivity of known biologically active glass and glass ceramics can be controlled very effectively by adding $TiO_2$ to the known composition even in a very small amount. Based upon the finding, we have found a novel composition of biologically active glass and glass ceramics useful for coating a metal core with the same to form implants. The novel composition has successfully broadened the selection range of reactivity for biologically active glass and glass ceramics.

For biologically active glass and glass ceramics hitherto proposed, a high content of $B_2O_3$ was required to attain the characteristic of low melting point. This resulted in an excess of reactivity so that any strong bonding between the biologically active material and bones could not be attained. In contrast, according to the invention, one can obtain biologically active glass and glass ceramics having the reactivity adjusted to a suitable level using $TiO_2$ even when a large amount of $B_2O_3$ must be contained in the biologically active material to satisify the requirement of low melting point.

Biologically active glass and glass ceramics according to the invention are essentially composed of:

| | | |
|---|---|---|
| $SiO_2$ | 5~60 | (by mol %) |
| $B_2O_3$ | 5~15 | |
| $Na_2O$ | 0~30 | |
| $CaO$ | 5~40 | |
| $TiO_2$ | 0.5~10 | |
| $P_2O_5$ | 0~15 | |
| $K_2O$ | 0~20 | |
| $Li_2O$ | 0~10 | |
| $MgO$ | 0~5 | |
| $Al_2O_3 + ZrO_2 + Nb_2O_5$ | 0~8 | |
| $La_2O_3 + Ta_2O_5 + Y_2O_3$ | 0~8 | and |
| $F_2$ | 0~15 | |

The biologically active material according to the invention includes all of the glass and glass-ceramics defined above. For the above composition it is unnecessary to differentiate glass from glass ceramics. As well known to those skilled in the art, glass can be crystallized into ceramics for the purpose of increasing its strength.

The above specified contents of the respective ingredients in the composition according to the invention are essential for the following reasons:

As mentioned above, $TiO_2$ is an essential ingredient to reduce the reactivity of the biologically active material. With a content above 10 mol% of $TiO_2$ the biologically active material can not have the desired characteristic of low melting point. Below 0.5 mol%, the reaction reducing effect of $TiO_2$ is too small to adjust the reactivity of the material to the desired level.

$B_2O_3$, $Na_2O$ and CaO have some effect on the reactivity although the effect is far smaller than that of $TiO_2$. The reactivity increases with increase of the content of these ingredients. Therefore, in case that the content of these ingredients is extremely high or extremely low, then it is impossible to adjust the reactivity to the desired level. For that reason, the content of $B_2O_3$ should be in the range of from 5 to 15 mol%. Similarly, the content of $Na_2O$ should be within the range of 10 to 30 mol% and that of CaO be within the range of 5 to 40 mol%.

$SiO_2$ is a network former. The reactivity of the biologically active material increases with decrease of the content of $SiO_2$. However, its effect on the reactivity is remarkably smaller than that of $TiO_2$. With a higher content of $SiO_2$ than 60 mol%, the material can not have the desired characteristic of low melting point. Below 35 mol% of $SiO_2$, it is impossible to adjust the reactivity of the material to the desired level even when it is controlled by $TiO_2$.

$K_2O$ and $Li_2O$ may be used in place of $Na_2O$ to control the reactivity and also to render the material fusible at relatively low temperatures. Above 10 mol% of $Li_2O$, the biologically active material loses its affinity for a living body.

MgO is substitutive for CaO. Above 5 mol% MgO, the composition loses its affinity for a living body.

$Al_2O_3$, $ZrO_2$ and $Nb_2O_3$ are substitutive for TiO. However, the content of these ingredients in total should be less than 8 mol%. Above 8 mol%, the biologically active material can not have the desired characteristic of low melting point.

$F_2$ serves to make the material fusible at relatively low temperatures. Above 15 mol% of $F_2$, it is impossible to give the composition an adequate reactivity.

A higher content than 8 mol% of $La_2O_3$, $Ta_2O_5$ and $Y_2O_3$ in total makes it impossible to render the material fusible at relatively low temperatures.

Above 15 mol% of $P_2O_5$, the material can not have any suitable reactivity.

Within the scope of the composition defined above, such glass and glass ceramics are particularly suitable for coating a metal core employing the enamelling process which are composed of:

| | | |
|---|---|---|
| $SiO_2$ | 40~60 | mol % |
| $B_2O_3$ | 8~15 | |
| $Na_2O$ | 15~30 | |
| CaO | 8~30 | |
| $TiO_2$ | 0.5~8 | |
| $P_2O_5$ | 0~8 | and |
| $F_2$ | 0~15. | |

Because of high content of $B_2O_3$, this group of glass and glass ceramics are fusible at temperatures low enough to apply the biologically active coating to a metal core by enamelling. In addition, because of a high content of $Na_2O$, the coating layer of this composition is tightly bonded to the core metal.

In contrast, biologically active glass and glass ceramics hitherto known have generally a high melting point even in the form of powder. Therefore, they are unsuitable for the enamelling process. When a coating of the known material is applied to a metal core, a large amount of metal ions are diffused into the glass so that the function of the coating as a biologically active material may be lost to a great extent.

The following examples illustrate the effect of the present invention.

EXAMPLES 1-4

Four different samples of glass and glass ceramics according to the invention were prepared as shown in Table 1. As for the contents of $B_2O_3$, $SiO_2$, $Na_2O$ and CaO, the four samples, Examples 1 to 4 were equal or approximately equal to each other. However, the content of $TiO_2$ was varied from sample to sample between 0.5 mol% and 3.0 mol%. The content of $B_2O_3$ in these examples is higher than that of the prior art biologically active glass and glass ceramics.

Measurements were conducted on the samples of Examples 1-4 to determine the coefficient of thermal expansion and the melting point in the form of powder. Values found are also given in Table 1.

TABLE 1

| | (mol %) | | | |
|---|---|---|---|---|
| Example No. | (1) | (2) | (3) | (4) |
| $SiO_2$ | 49.5 | 49.0 | 48.5 | 48.5 |
| $B_2O_3$ | 12.0 | 12.0 | 12.0 | 11.0 |
| $Na_2O$ | 23.0 | 23.0 | 22.5 | 22.5 |
| CaO | 15.0 | 15.0 | 15.0 | 15.0 |
| $TiO_2$ | 0.5 | 1.0 | 2.0 | 3.0 |
| Coefficient of thermal expansion ($10^{-7}$ °C.$^{-1}$) | 130 | 130 | 130 | 130 |
| Melting point as powder (°C.) | 690 | 690 | 690 | 695 |

As seen in Table 1, the biologically active glass and glass ceramics exhibited the same coefficient of thermal expansion. Their melting points as powder were very low which were 690° C. and the vicinity of 690° C. Furthermore, as seen in FIG. 1, the reactivity of the biologically active material was successfully changed by changing the content of $TiO_2$.

FIG. 1 shows changes of pH of a simulated physiological solution with time for above Examples 1-4 shown in Table 1. Curves (1), (2), (3) and (4) were obtained from the compositions of Examples 1, 2, 3 and 4 respectively in the following procedure:

Each sample was immersed in a simulated physiological solution and held immersed for a long time during which pH of the solution was continuously measured. Found values of pH were then plotted as shown in FIG. 1 with the pH of the solution as the ordinate and the treating time (hr.) in logarithmic notation as the abscissa.

FIG. 1 indicates that the highest value of pH was obtained for the composition of Example 1 in which the content of $TiO_2$ was the smallest of all the four compositions and that the lowest pH was for the composition of Example 4 having the largest content of $TiO_2$ of all. This demonstrates that the reactivity of the biologically active material according to the invention can be controlled effectively by changing the content of $TiO_2$. The degree of increase of pH becomes smaller as the content of $TiO_2$ is increased and therefore it is obvious that the reactivity of the material to a living body can be reduced by increasing the content of $TiO_2$.

The biologically active glass of Example 1 which exhibited the highest reactivity in the above pH test was shaped into a cylinder of 1 mm in diameter×3 mm in length. The cylinder was implanted in a thighbone of a rat where the level of bone forming ability is relatively high. On the other hand, the biologically active glass of Example 3, the reactivity of which was found to be relatively low, was shaped into a cylinder of 3 mm in diameter×5 mm in length. The cylinder was implanted in the jawbone of a dog where the level of bone forming ability is relatively low. In both of the two experiments in vivo, there was obtained a strong glass-to-bone bond.

For the purpose of comparison, a known biological active material disclosed in the above referred to patent publication, Japanese Patent Application Laid Open No. 145,394/1978 and named "Bioglass A" was tested in the same manner as above. Although the known material exhibited a high bonding strength to the thighbone of a rat, the bonding obtained between the material and the jawbone of a dog was poor in strength.

Biologically active material known from the above referred to patent publication have high melting points as powder which were measured to be about 1100° C. or higher. This is far higher than that of the materials according to the present invention. It is possible to lower the high melting point to some extent by adding $B_2O_3$ to the known composition. However, addition of $B_2O_3$ more than 10 mol% causes the known composition to have an excess reactivity. In this case, unlike the material according to the invention, it is very difficult to adjust the reactivity to a desired level.

For Examples 1 to 4, the following weight % equivalent apply:

| Example | (1) | (2) | (3) | (4) |
| --- | --- | --- | --- | --- |
| $SiO_2$ | 48.6 | 48.1 | 47.4 | 47.4 |
| $B_2O_3$ | 13.7 | 13.6 | 13.6 | 12.4 |
| $Na_2O$ | 23.3 | 23.3 | 22.7 | 22.6 |
| CaO | 13.8 | 13.7 | 13.7 | 13.7 |
| $TiO_2$ | 0.6 | 1.3 | 2.6 | 3.9 |

EXAMPLES 5-8

Further examples are shown in Table 2 as Examples 5-8.

TABLE 2

| Example No. | (mol %) | | | |
| --- | --- | --- | --- | --- |
| | (5) | (6) | (7) | (8) |
| $SiO_2$ | 48.0 | 47.5 | 47.0 | 47.0 |
| $B_2O_3$ | 12.0 | 12.0 | 12.0 | 11.5 |
| $Na_2O$ | 23.0 | 23.0 | 23.0 | 23.0 |
| CaO | 12.5 | 12.5 | 12.5 | 12.5 |
| $CaF_2$ | 2.0 | 2.0 | 2.0 | 2.0 |
| $AlF_3$ | 2.0 | 2.0 | 2.0 | 2.0 |
| $TiO_2$ | 0.5 | 1.0 | 1.5 | 2.0 |
| Coefficient of thermal expansion ($10^{-7}$ °C.$^{-1}$) | 135 | 135 | 135 | 135 |
| Melting point as powder (°C.) | 670 | 670 | 670 | 675 |

This group of biologically active compositions shown in Table 2 contains fluorides in addition to the ingredients shown in Table 1. Fluorides serve to reduce the reactivity of the biologically active composition as a whole as seen in FIG. 2 showing the change of pH with time similarly to FIG. 1. The reduced reactivity is further adjusted to a desired level by changing the content of $TiO_2$ (See FIG. 2). These compositions have the same coefficient of thermal expansion, which makes it convenient to coat the same kind of metal cores with different biologically active compositions. The melting points of this group of biologically active compositions in the form of powder are all low which are about 670° C.

For examples 5 to 8, the following weight % equivalents apply:

| Example | (5) | (6) | (7) | (8) |
| --- | --- | --- | --- | --- |
| $SiO_2$ | 46.4 | 45.9 | 45.3 | 45.3 |
| $B_2O_3$ | 13.5 | 3.4 | 3.4 | 2.8 |
| $Na_2O$ | 23.0 | 22.9 | 22.9 | 22.9 |
| CaO | 11.3 | 11.3 | 11.3 | 11.2 |
| $CaF_2$ | 2.5 | 2.5 | 2.5 | 2.5 |
| $AlF_3$ | 2.7 | 2.7 | 2.7 | 2.7 |
| $TiO_2$ | 0.6 | 1.3 | 1.9 | 2.6 |

EXAMPLES 9-12

Still further examples of preferred biologically active glass and glass-ceramic compositions are shown in Table 3 as Examples 9-12.

This group of compositions contain some further ingredients in addition to the ingredients shown in Table 2.

$K_2O$ and $Li_2O$ may be added in place of $Na_2O$ to attain the same effect. $Al_2O_3$, $ZrO_2$ and $Nb_2O_5$ have the effect of controlling the reactivity of biologically active material and therefore may be used to assist $TiO_2$ in controlling the reactivity. Addition of $La_2O_3$, $Ta_2O_5$ and $Y_2O_3$, even in a very small amount, produces such biologically active glass and glass ceramics which exhibit a high X-ray absorption coefficient which makes it easy to observe the implant after implantation. Addition of $P_2O_5$ has the effect of improving the affinity of the material to a living body. MgO has a similar function to CaO and therefore it is substitutive for CaO.

TABLE 3

| Example No. | mol % | | | |
| --- | --- | --- | --- | --- |
| | (9) | (10) | (11) | (12) |
| $SiO_2$ | 48.0 | 48.0 | 47.5 | 46.0 |
| $B_2O_3$ | 12.0 | 2.0 | 12.0 | 1.0 |
| $Na_2O$ | 21.5 | 1.5 | 21.0 | 20.0 |
| CaO | 15.0 | 0.0 | 15.0 | 3.5 |
| $TiO_2$ | 1.0 | .0 | 0.5 | .0 |
| $P_2O_5$ | 2.5 | 2.5 | 2.5 | 2.5 |
| $K_2O$ | — | 0.0 | — | — |
| $Li_2O$ | — | 2.0 | — | — |
| $Al_2O_3$ | — | — | 1.5 | — |
| $ZrO_2$ | — | — | 1.5 | — |
| $Nb_2O_5$ | — | — | 1.5 | — |
| $La_2O_3$ | — | — | — | 1.0 |
| $Ta_2O_5$ | — | — | — | 1.0 |
| $Y_2O_3$ | — | — | — | 1.0 |
| MgO | — | 2.0 | — | — |
| Coefficient of thermal expansion ($10^{-7}$ °C.$^{-1}$) | 130 | 20 | 30 | 35 |
| Melting point as powder (°C.) | 690 | 690 | 700 | 740 |

This group of compositions shown in Table 3 also has the desired characteristic of low melting point. Further, as seen in FIG. 3, all of the compositions showed the desired level of reactivity. The reactivity can be further finely controlled by changing minutely the contents of $TiO_2$, $Al_2O_3$, $ZrO_2$ and $Nb_2O_5$ serving as reaction controller.

The glass and glass ceramics according to the invention can be applied to a metal core to form an implant. The metal core to be covered with a coating of the biologically active material may be made of any suitable metal such as stainless steel, cobalt-chromium alloy, titanium, titanium alloy, noble metals, for example, platinum, noble metal alloy, for example, platinum (90%)-rhodium (10%) alloy or molybdenum-nickel-cobalt-chromium alloy. Preferably the coating layer is 0.1 to 2 mm thick. Coating may be carried out employing a suitable known coating process such as enamelling and sealing.

Therefore, the present invention includes also such metal implants coated with the above defined glass and glass ceramics. The following examples, Example 13 is given to illustrate the implant according to the invention.

For examples 9 to 12, the following weight % equivalents apply:

| Example | (9) | (10) | (11) | (12) |
|---|---|---|---|---|
| $SiO_2$ | 45.6 wt. % | 45.0 wt. % | 44.1 wt. % | 34.8 wt. % |
| $B_2O_3$ | 13.2 | 13.0 | 12.9 | 9.6 |
| $Na_2O$ | 21.1 | 6.3 | 20.1 | 15.6 |
| CaO | 13.3 | 8.8 | 13.0 | 9.5 |
| $TiO_2$ | 1.2 | 1.3 | 0.6 | 1.0 |
| $P_2O_5$ | 5.6 | 5.5 | 5.5 | 4.5 |
| $K_2O$ | — | 14.7 | — | — |
| $Li_2O$ | — | 2.3 | — | — |
| $Al_2O_3$ | — | — | 0.8 | — |
| $ZrO_2$ | — | — | 0.9 | — |
| $Nb_2O_5$ | — | — | 2.1 | — |
| $La_2O_3$ | — | — | — | 8.2 |
| $Ta_2O_5$ | — | — | — | 11.1 |
| $Y_2O_3$ | — | — | — | 5.7 |
| MgO | — | 3.1 | — | — |

EXAMPLE 13

A cylindrical metal core of 5 mm in diameter and 10 mm in length was formed of an alloy comprising:

| | |
|---|---|
| Ni | 59 wt. % |
| Cr | 15 |
| Co | 15 |
| Mo | 7 and |
| others | 4. |

The cylindrical metal core was then subjected to a sandblast treatment by alumina particles of 180 grit under the pressure of 8 kg/cm². This surface treatment is useful for reinforcing the bonding strength of glass-to-metal chemical bond by the aid of mechanical bond.

Following the surface treatment, the core was subjected to a supersonic cleaning in acetone for three minutes. The metal core was then held in vacuum over $10^{-6}$ Torr at 800° C. for a half hour for degassing. This degassing has the effect of preventing bubbling from the surface of the core when it is brought into contact with molten glass of high temperature.

The glass composition of Example 1 described above was milled into powder whose particle size was less than 200 mesh. The powdered glass was then mixed with the same volume of a solvent mixture such as 10:1 by volume mixture of ethanol and triethanolamine to form a slurry. The slurry was applied to the pretreated metal core by dipping or coating to produce a slurry layer about 3 mm thick on the metal core with its one end surface being left uncoated.

The metal core carrying the layer of slurry coating was placed within a heating furnace. The temperature in the furnace was raised from room temperature to 680° C. in a half hour and held at 680° C. for three minutes. During this period of heating, organic materials contained in the slurry layer were all vaporized or burnt off and the molten fine glass particles bonded together so as to form a glass coating layer covering the metal core. The coated metal core was then transferred into another heating furnace being held at 450° C. After leaving the coated metal core standing in the furnace for five hours or more, it was cooled to the room temperature. Thus, an implant comprising a metal core and a coating layer of biologically active glass was prepared.

If desired, the implant thus prepared may be further treated by holding it at a temperature ranging from 600° to 700° C. for about an hour to cause a phase separation or a crystal phase formation in the glass coating layer.

As understood from the foregoing, the present invention brings forth various advantages over the prior art.

According to the invention, any desired combination of reactivity and thermal expansion coefficient may be selected for biologically active glass and glass ceramics by suitably selecting the content of $TiO_2$. Therefore, the present invention permits the preparation of many biologically active materials having different reactivity levels for a kind of metal core. Thus, by coating metal cores made of the same kind of metal with differently reactive biologically active materials there can be provided various implants having different reactivities. The operator, therefore, can select a most suitable implant for a patient who undergoes an implanting operation while considering the bone forming ability determined by the age and condition of the patient as well as position at which the implant is to be located. This always assures a better solution than does the prior art.

Another advantage of the biologically active materials according to the invention resides in lower melting point. Owing to the characteristic of low melting point, the coating material can be applied to a metal core employing the preferred enamelling process which provides a high quality and uniform coating at a higher work efficiency. Since a uniform coating can be obtained, work on the implant after coating can be done very easily.

Implants coated with the glass and glass ceramics according to the invention are tightly bonded to bones. Therefore, they are useful, for example, as a substitute material for bone, bone reinforcing material and dental roots. It is evident that the present invention makes a great contribution to medicine.

We believe that the preparation and use of our biologically active glass and glass ceramics composition will now be understood and that the several advantages thereof will be fully appreciated by those persons skilled in the art.

We claim:

1. An improved implant comprising a biocompatible metal core coated with a layer of a biologically active glass or glass-ceramic having a composition consisting essentially of by mol%:

| | |
|---|---|
| $SiO_2$ | 40-60 |

-continued

| | |
|---|---|
| $B_2O_3$ | 8–15 |
| $Na_2O$ | 15–30 |
| $CaO$ | 8–30 |
| $P_2O_5$ | 0–8 |
| $K_2O$ | 0–20 |
| $Li_2O$ | 0–10 |
| $MgO$ | 0–5 |
| $Al_2O_3 + ZrO_2 + Nb_2O_5$ | 0–8 |
| $La_2O_3 + Ta_2O_5 + Y_2O_3$ | 0–8 and |
| $F_2$ | 0–15 | the glass or glass-ceramic having substantially the same thermal expansion coefficient as that of the metal core, wherein the improvement comprises adding $TiO_2$ in an amount from 0.5 to 3 mole% to make up a total of 100 mol% glass composition to regulate the degree of biological activity of the glass or glass-ceramic represented by a saturated pH-value at the time when the glass or glass-ceramic is immersed in a simulated physiolgical solution, with no substantial change of the thermal expansion coefficient of the glass or glass-ceramic.

2. The implant of claim 1 wherein said $TiO_2$ is added in amounts from 0.5 to 1 mol%.

3. An implant as set forth in claim 1, wherein said coating layer of biologically active composition is 0.1 to 2 mm thick.

* * * * *